(12) United States Patent
Stewart

(10) Patent No.: US 9,352,469 B2
(45) Date of Patent: May 31, 2016

(54) ROBOTIC DISINFECTION SYSTEM

(71) Applicant: Michael Stewart, Detroit, MI (US)

(72) Inventor: Michael Stewart, Detroit, MI (US)

( * ) Notice: Subject to any disclaimer, the term of this patent is extended or adjusted under 35 U.S.C. 154(b) by 0 days.

(21) Appl. No.: 14/269,837

(22) Filed: May 5, 2014

(65) Prior Publication Data

US 2014/0330452 A1    Nov. 6, 2014

Related U.S. Application Data

(60) Provisional application No. 61/819,191, filed on May 3, 2013.

(51) Int. Cl.
| | |
|---|---|
| *B25J 11/00* | (2006.01) |
| *G05D 1/00* | (2006.01) |
| *G05D 1/02* | (2006.01) |
| *A61L 2/10* | (2006.01) |
| *B25J 5/00* | (2006.01) |
| *B25J 9/08* | (2006.01) |
| *B25J 19/02* | (2006.01) |

(52) U.S. Cl.
CPC .............. *B25J 11/0085* (2013.01); *B25J 5/007* (2013.01); *B25J 9/08* (2013.01); *B25J 19/02* (2013.01); *A61L 2/10* (2013.01); *Y10S 901/01* (2013.01)

(58) Field of Classification Search
USPC .................................. 701/2, 3–28; 901/1–13
See application file for complete search history.

(56) References Cited

U.S. PATENT DOCUMENTS

| | | | | |
|---|---|---|---|---|
| 5,959,423 | A * | 9/1999 | Nakanishi ............. | A47L 11/305 15/319 |
| 2005/0000543 | A1* | 1/2005 | Taylor .................. | G05D 1/0219 134/18 |
| 2005/0010331 | A1* | 1/2005 | Taylor .................. | G05D 1/0219 700/245 |
| 2006/0020369 | A1* | 1/2006 | Taylor ..................... | A47L 9/009 700/245 |
| 2007/0061040 | A1* | 3/2007 | Augenbraun ........... | A47L 5/225 700/245 |
| 2012/0313014 | A1* | 12/2012 | Stibich ...................... | A61L 2/10 250/492.1 |
| 2012/0313532 | A1* | 12/2012 | Stibich ...................... | A61L 2/10 315/150 |
| 2013/0270459 | A1* | 10/2013 | Fontani ..................... | A61L 2/10 250/492.1 |
| 2014/0061509 | A1* | 3/2014 | Shur ....................... | A23L 3/003 250/492.1 |
| 2014/0158917 | A1 | 6/2014 | Stibich et al. | |

* cited by examiner

*Primary Examiner* — Rami Khatib
*Assistant Examiner* — Timothy Nesley
(74) *Attorney, Agent, or Firm* — Harness, Dickey & Pierce, P.L.C.

(57) ABSTRACT

A robotic platform is provided having a disinfection unit configured to disinfect a technical area.

16 Claims, 6 Drawing Sheets

ROBOTIC DISINFECTION SYSTEM

CROSS-REFERENCE TO RELATED APPLICATIONS

This application claims the benefit of U.S. Provisional Application No. 61/819,191, filed on May 3, 2013. The entire disclosure of the above application is incorporated herein by reference.

FIELD

The present disclosure relates to a mobile robotic platform and, more particularly, to a mobile robotic platform having a U.V. emitting disinfection unit.

BACKGROUND

This section provides background information related to the present disclosure which is not necessarily prior art. Various disinfection and servicing tasks in large technical facilities, such as operating theaters, require different types of fluid application which is difficult. Automatic disinfecting systems must be designed and constructed specifically for the respective purpose.

SUMMARY

This section provides a general summary of the disclosure, and is not a comprehensive disclosure of its full scope or all of its features.

The present disclosure is directed to a robot platform, for remotely controlled and/or autonomous disinfection of technical facilities. The robot platform includes at least a drive mechanism configured to move the robot platform; a disinfection device configured to disinfect the technical facility; a position determination device configured to determine position data of the robot platform, and a communication device configured to exchange measurement and/or control data and transmission of measurement and position data to an evaluation unit.

In one embodiment of the robot platform according to the present teachings, the robot platform is formed from individual modules which are physically connected to one another by mechanical connectors.

According to another embodiment, individual modules each have one or more submodules. In particular, one of the submodules is an interface for data exchange and the power supply link between the modules. In a still further embodiment, individual modules have an electric drive motor and an integrated control unit for the electric drive motor, which control unit has a power submodule and a microcontroller submodule as submodules. According to another embodiment, at least one of the modules is a drive module for movement of the robot platform.

In one development of this embodiment, at least one drive module has an electric drive motor, in particular a direct-current motor, and, as submodules, has at least one U.V. transmitter which disinfects a surface of the technical facility to be disinfected, a power submodule for supplying power to the drive motor, and a microcontroller submodule for controlling the electric drive motor. In another embodiment of the invention, one of the modules is in the form of a linear movement module for linear movement of a disinfection device arranged on it.

In yet another embodiment of the invention, one of the modules is a base station, which is provided in order to move the disinfection module and control the disinfection signals.

In another embodiment, a device that coordinates transformation of the position data is provided upstream of the evaluation unit, such that the evaluation unit can operate in a freely selectable coordinate system which is matched to the disinfection task.

In a further embodiment of the invention, at least one of the modules is designed to determine the position of the robot platform. In one development of this embodiment, a position transmitter submodule is provided to determine the position, and has a position transmitter wheel and an encoder unit.

In one embodiment of the robot platform according to the invention, the robot platform is formed from individual modules which are physically connected to one another by mechanical connectors and/or for exchanging data by digital communication links, which operate in accordance with a uniform standard.

According to another embodiment, individual modules each have one or more submodules. In particular, one of the submodules is an interface for data exchange and the power supply link between the modules. In a still further embodiment, individual modules have an electric drive motor and an integrated control unit for the electric drive motor, which control unit has a power submodule and a microcontroller submodule as submodules. According to another embodiment, at least one of the modules is a drive module for movement of the robot platform.

In one development of this embodiment, the at least one drive module has an electric drive motor, in particular a direct-current motor, and, as submodules, has at least one magnet wheel for rolling on and sticking to a surface, which can be magnetized, of the technical facility to be disinfected, a power submodule for supplying power to the drive motor, and a microcontroller submodule for controlling the electric drive motor. In another embodiment of the invention, one of the modules is in the form of a linear movement module for linear movement of a disinfection device arranged on it.

In yet another embodiment of the invention, one of the modules is a base station, which is provided in order to control the data interchange of disinfection signals with the other modules and evaluation units. In another embodiment, the base station emulates encoder signals, in order to allow simple connection of evaluation units to the robot platform. In another embodiment, a device that coordinates transformation of the position data is provided upstream of the evaluation unit, such that the evaluation unit can operate in a freely selectable coordinate system which is matched to the disinfection task.

In a further embodiment of the invention, at least one of the modules is designed to determine the position of the robot platform. In one development of this embodiment, a position transmitter submodule is provided to determine the position, and has a position transmitter wheel and an encoder unit.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure. The invention will be explained in more detail in the following text, using exemplary embodiments and in conjunction with the drawing, in which.

Corresponding reference numerals indicate corresponding parts throughout the several views of the drawings.

DETAILED DESCRIPTION

Figure 1:
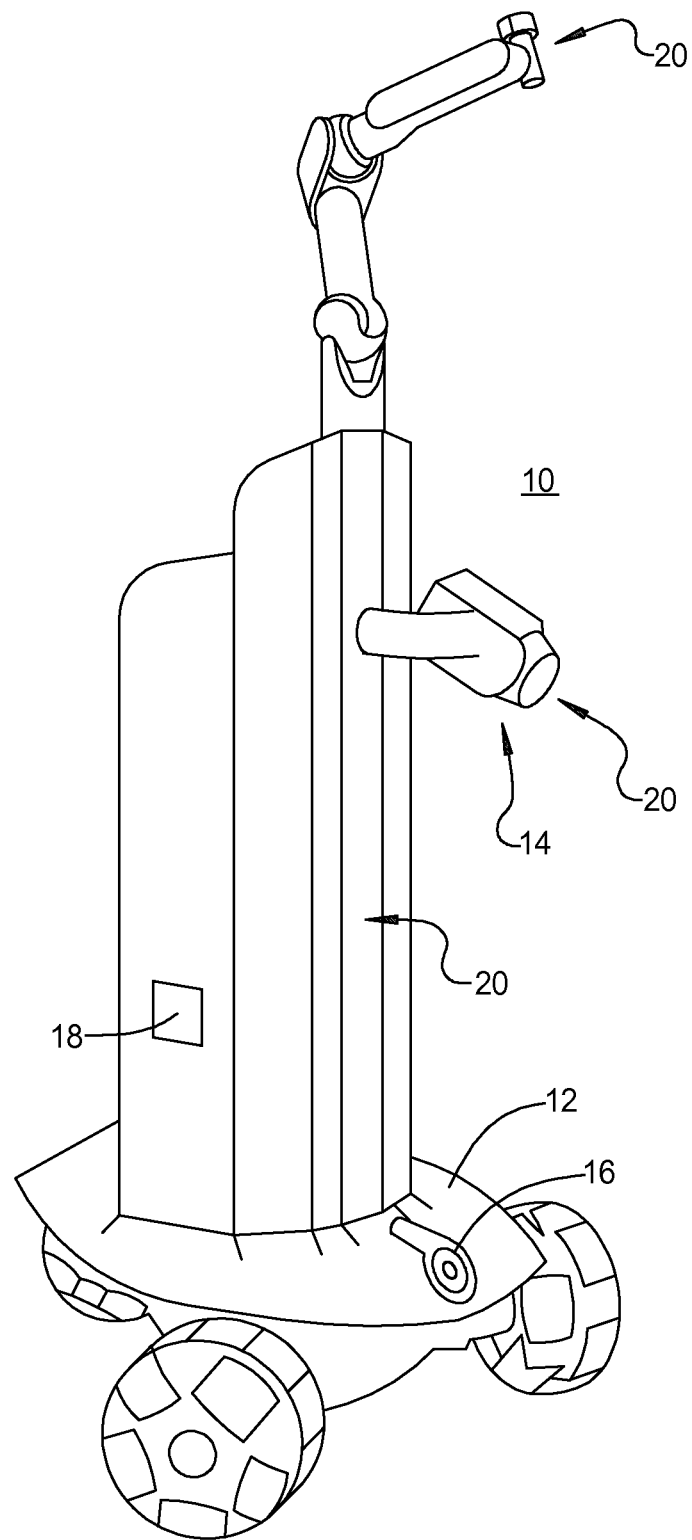
FIG. 1 shows a modular robot platform according to one exemplary embodiment of the invention.

Example embodiments will now be described more fully with reference to the accompanying drawings. An object of the invention is to provide a robot platform for a disinfection system, which avoids the disadvantages of known disinfection units and provides a substantial broadening of the capability for matching to different disinfection tasks and scenarios. The object is achieved by the system described in the appended claims.

As shown in FIGS. 1-4, the robot platform according to the present teachings, is intended in particular for remotely controlled and/or autonomous disinfection of technical facilities, in particular in operating theaters, and comprises at least a drive mechanism that moves the robot platform; an disinfection device that disinfects the technical facility; a device to determine position data of the robot platform, and a communication device to exchange measurement and/or control data and transmission of measurement and position data to an evaluation unit. The robot platform is modular, in that the communication device operates in accordance with a uniform standard, and the measurement and position data is streamed to an evaluation unit sufficiently quickly that the time delay is sufficiently short for contamination-free disinfection.

The present invention proposes a robot platform 10 which is designed as a modular system and can therefore be adapted to widely differing purposes depending on the choice and configuration of the individual modules. This modular system is distinguished by the following characteristics and advantages: the system comprises a base module 12, and application-specific parts 14 are added to it, for example, sensors 16 where necessary, a control unit 18 is integrated in the base module 12 and provides the local intelligence required for operation of the module each module has a standardized interface for connection to other modules and/or to a base unit which is located outside the location which is to be disinfected. The laser line sensors can be used to plot a room to determine if surfaces are not visible from the disinfecting module. The path of the robot can programmed so as to minimize the amount of non-radiated surfaces.

FIG. 1 shows a design of a modular robot platform according to one exemplary embodiment of the teachings. The robot platform in FIG. 1 has a base module, which is connected to components to form the robot platform by physical connectors (for example screw connections) which are not specified in any more detail. Each of the modules itself has a plurality of submodules, which are characteristic of the design and function of the respective module.

Modules can exchange data directly with one another via standardized communication links, which can, for example, operate in accordance with the Ethernet standard. Appropriate interfaces are provided in the modules in order to allow this data interchange. If necessary, the submodules in the individual modules can also exchange data via corresponding communication links. Furthermore, a communication link is provided between the robot platform and a base station, via which commands can be sent to the robot platform 10, and position data can be received from the robot platform 10.

Because of the modular design of the robot platform 10 and the internal communication capabilities by Ethernet between the modules and the submodules, there is sufficient intelligence in the robot platform itself to allow open-loop control, closed-loop control and measurement processes to be carried out autonomously internally without having to handle a data interchange, which is sensitive to interference, with the base station.

The robot platform has a sterilizing module 20. The sterilizing module 20 can be formed of an array of ultraviolet emission bulbs or LEDs disposed within the body of the mobile platform 10. It is envisioned the platform 10 can be tall enough so to position the light emitters above horizontal surfaces to be disinfected. In this regard, the mobile platform can be higher than, for example, 7 feet. The sterilizing module can have selectively engagable shields which function to block the application of UV radiation in a specific direction. The shields can be adaptable is size so the location of the illumination can vary as the platform moves through a technical area. Optionally, the sterilizing module can have selectively engagable lenses to focus UV energy into areas. The disinfecting unit 20 can spray liquid disinfectant from for example the base to sterilize surrounding surfaces such as a floor.

Figure 2:
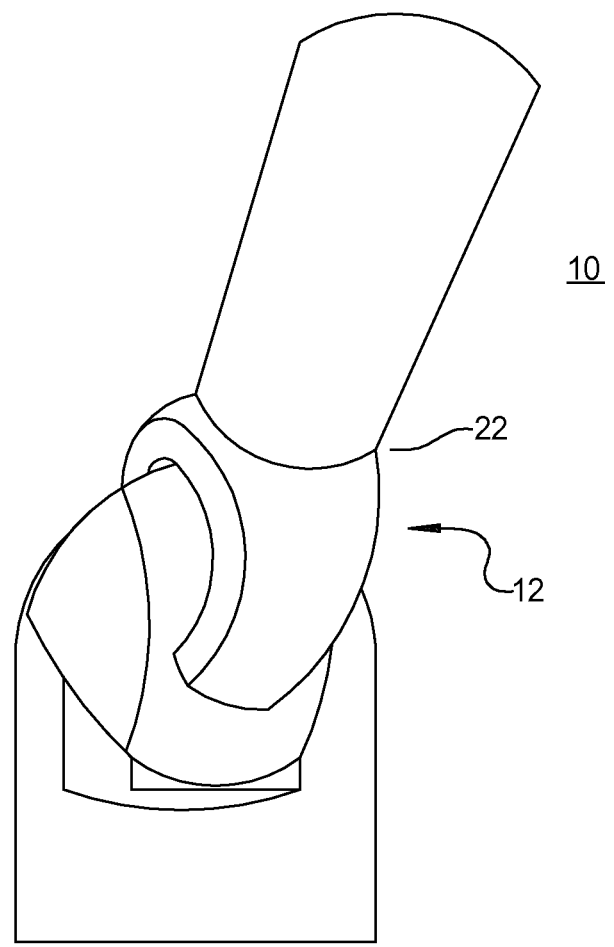
FIG. 2 shows a perspective view of a robot platform having two drive modules and a movement module, according to another exemplary embodiment of the invention.
Figure 3:
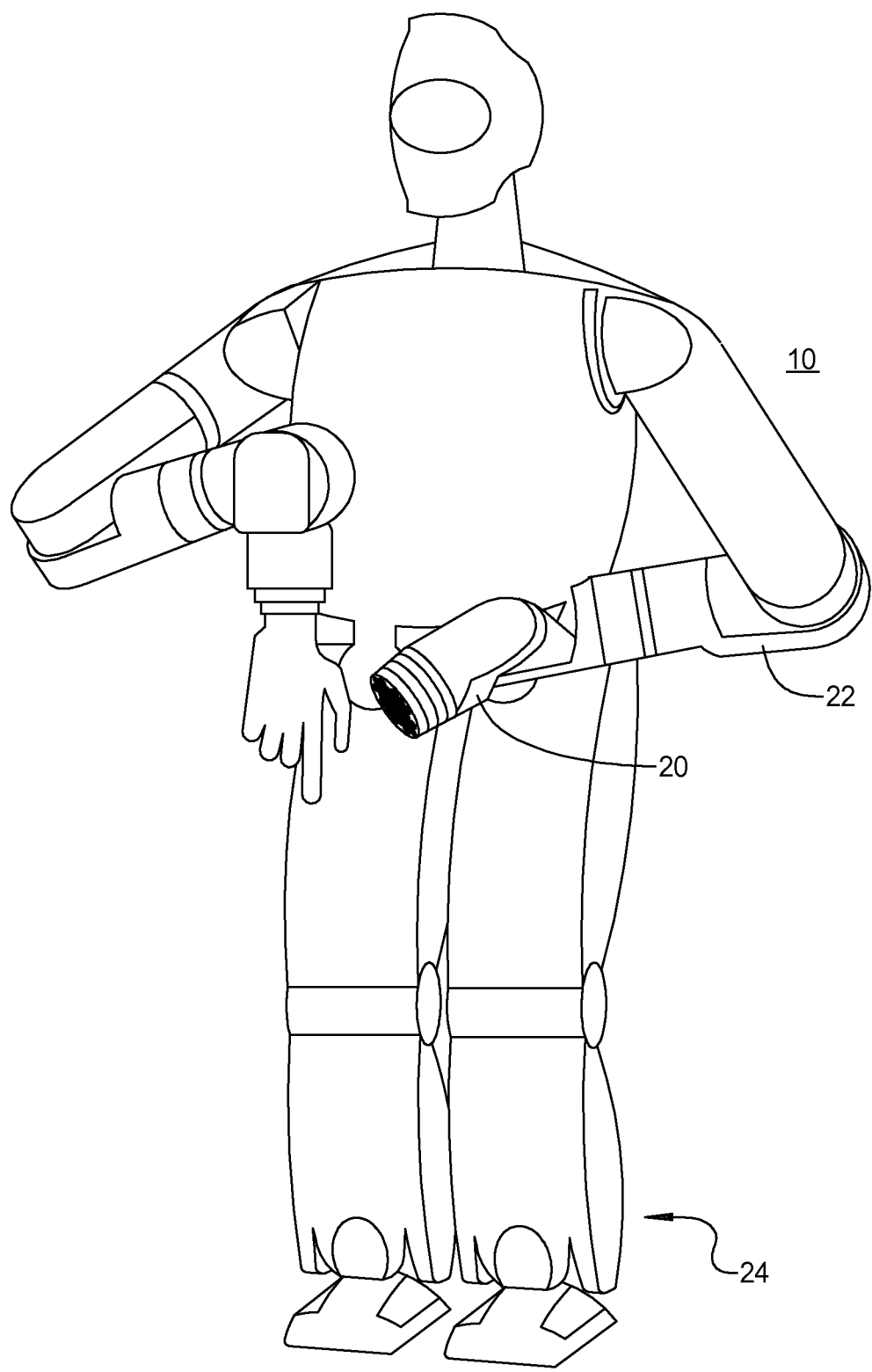
FIG. 3 shows a mobile robot platform according to the present teachings.
Figure 4:
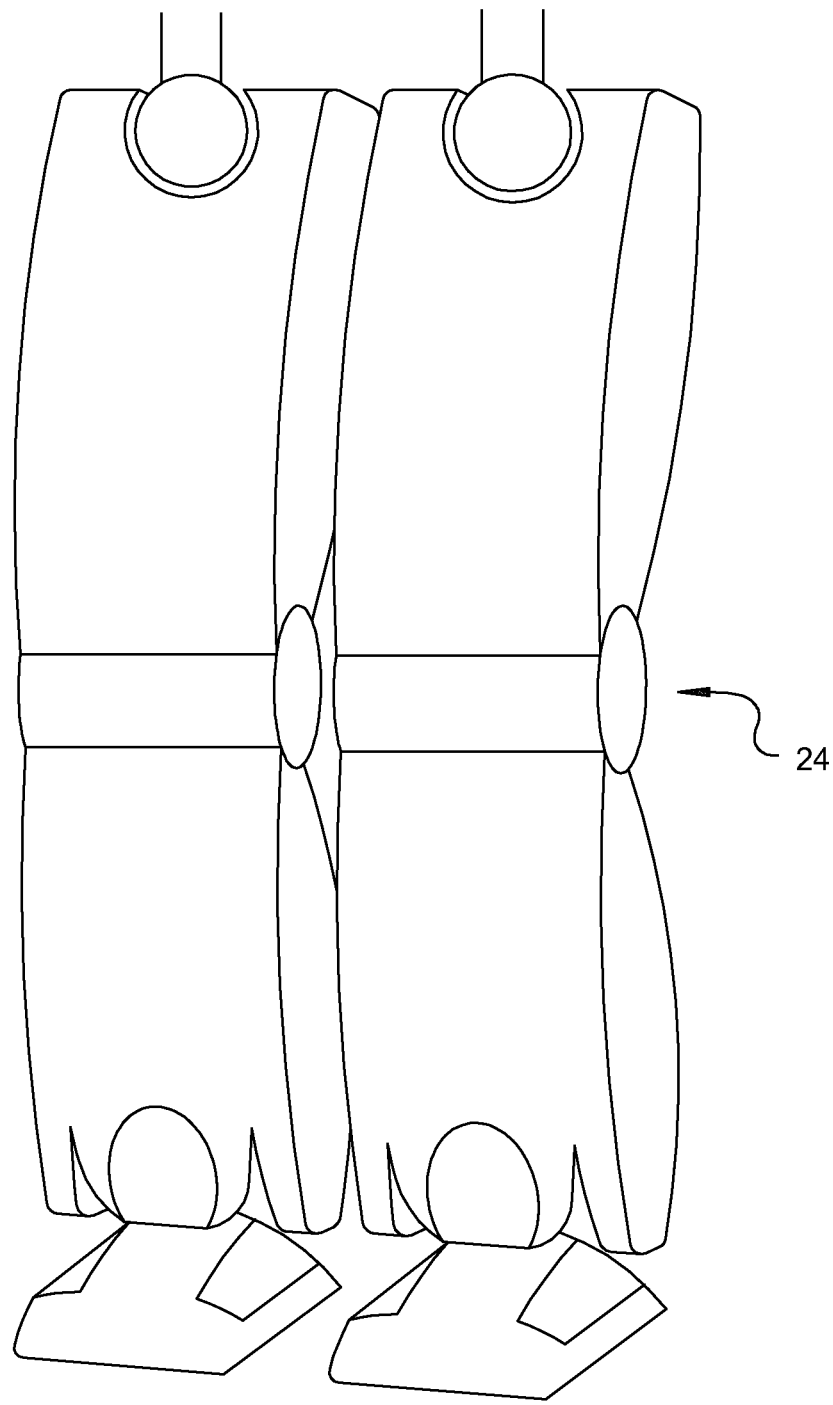
FIG. 4 represents the leg assembly of the mobile platform shown in FIG. 3.

As shown in FIGS. 2 and 3, the platform 10 can have an articulating arm 22 which has an associated disinfecting module 20. The articulating arm 22 has actuators 24 which can direct the emissions from the disinfecting module 20 toward locations which may not be "visible" to emissions from disinfecting modules 20 fixed to the platform 10.

FIG. 3 illustrates one example of a specific robot platform designed on the basis of these principles. The robot platform shown there comprises two drive modules of the same type, which are arranged at a distance from one another and are responsible for controlled movement of the robot platform.

The drive module 24 can be an elongated module with a largely cuboid geometry and, at one end, and can have a pair of wheels which are arranged off-center such that the drive module 24 can be used for propulsion in a robot platform both in the vertical position and in the horizontal position. The wheels on the one hand roll on a base when the robot platform is moved on the base. By way of example, this allows a robot platform 10 to be moved around a rotor shaft of a turbine without falling down or sliding off.

A direct-current motor is arranged in the interior of the drive module and drives the magnetic wheels via a gearbox. A power submodule is provided to supply electricity to the direct-current motor and, for example, may be in the form of a printed circuit board (PCB), and contains the electronic components (power semiconductors, capacitors, resistors, etc.) which are required to drive the motor. In addition to the power submodule, a microcontroller submodule with a microcontroller is also accommodated in the drive module. The microcontroller submodule controls the operation of the direct-current motor on the basis of the measured actual position and the desired nominal position of the robot platform. In the simplest case, an appropriate encoder can be fitted to the wheels themselves, the encoder measures the revolution of the wheels and emits appropriate data to the microcontroller. In addition, the microcontroller submodule may provide further data inputs and outputs, for example in order to allow switches or sensor data to be read in or display elements to be controlled. Such additional functionalities can easily be achieved by a control program which runs on the microcontroller.

If the aim is to avoid faults associated with slip when determining position, the robot platform may be equipped with an autonomous position transmitter submodule, which uses a specific position transmitter wheel to record the distance traveled, largely without slip, and makes this available as position data via an encoder unit which is accommodated in the chassis. The position submodule can be fitted to a suitable point on the robot platform by a universal mounting element. The microcontroller is designed such that it can read and process or pass on these additional signals without major complexity. In addition to drastically reducing positioning error, this position submodule therefore also makes it possible to implement slip monitoring and to provide an appropriate warning to the superordinate program or the operator.

The two drive modules, which are at a distance from one another, are firmly connected to one another by a linear movement module in the robot platform as shown in FIG. 1 and FIG. 3. A carriage is arranged such that it can move longitudinally on this linear guide. The carriage is designed for sensor units to be fitted to it, and is therefore equipped with appropriate mounting holes. The carriage can be moved via a motor, which is accommodated in the linear movement module associated with the elongated members, but is not illustrated in FIG. 2 in such a way that the sensor which is mounted on it allows movement transversely with respect to the direction of travel. In this case as well, appropriate submodules for operation of the motor are accommodated in the module.

In the present case, a (passive) steering roller is mounted as a further module on the underneath of the electronics box and supports the robot platform 10, such that it can move, in the area of the projecting electronics box. The steering roller has two wheels which are arranged parallel and are mounted via a rotating bearing such that they can rotate about a vertical axis. A roller such as this can advantageously be used for steering the robot platform, when combined with an appropriate servo module. Another steering option is provided by differentially driving to the two drive modules.

Overall, a modular robot platform for disinfection and servicing of technical facilities according to the invention is distinguished in that it has at least one drive unit with integrated control electronics it has a device to determine the position of the robot platform, The individual modules have standardized digital interfaces for intermodular data interchange, and the position data from the unit is transmitted to the exterior via digital interface for further use outside the control loop of the motor drive, and is made available for further purposes.

As shown the robotic platform can take any form, for example a humanoid form having articulated hand for grasping and moving objects, articulated legs, knees, waist and neck. The platform can provide directional U.V. and laser light for sterilization and can generate ions for sterilization. Optionally, the system can generate ions and direct to surface or blanket ion emissions for surface disinfection and sterilization. It is envisioned the platform can have sonar, IR and laser range finding navigation transceivers which can map room and surfaces, generate topographical 3D map for robot navigation and surface sterilization. Additionally, the platform can provide sensing devices such as a spectrometer to measure airborne bacteria, molds and viruses to apply unidirectional U.V. and laser sterilization. Optionally, the system can utilize optical or infra-red sensors to enable automatic safety shutoff upon encountering a human or a human shape.

Additionally, the system can have pre-defined routines which allow for the disinfection of medical devices. This shutoff system can also optionally detect the remote opening of a door into the technical area.

The self-propelled mobile platform can be self-decontaminating, self-controlled, have processors which allow for adaptive learning. Optionally, the mobile platform can be wirelessly remote control from operator and can include an imaging device such as a color stereo and 3D cameras to allow an operator to remotely clean an area. Optionally, the wireless control, communication and data transfer can occur from one robot to another to teach one another.

An onboard computer can be used for direct access or web based control of the robot. The mobile platform can respond to voice commands and control, can be speech capable. Navigation can occur using a pre-map area or operating theater. Optionally, motion sensors to track object movement within the disinfecting area. The disinfecting unit can be fixed lamps incorporated into the body of the mobile platform or can be lamps affixed to movable appendages associated with the robot. These appendages can include high degree of freedom in robot joints.

The rooms being disinfected can include tracking and locating beacons to facilitate movement of the mobile platform. Optionally, robots can be located and positioned by GPS. Further, the room can include self-docking in a recharging dock station. The enclosed docking station can be used for self-decontamination and self-maintenance, sense internal status. For example, low battery, needs to self-dock to recharge. Run diagnostic programs for operating errors.

Figure 5:
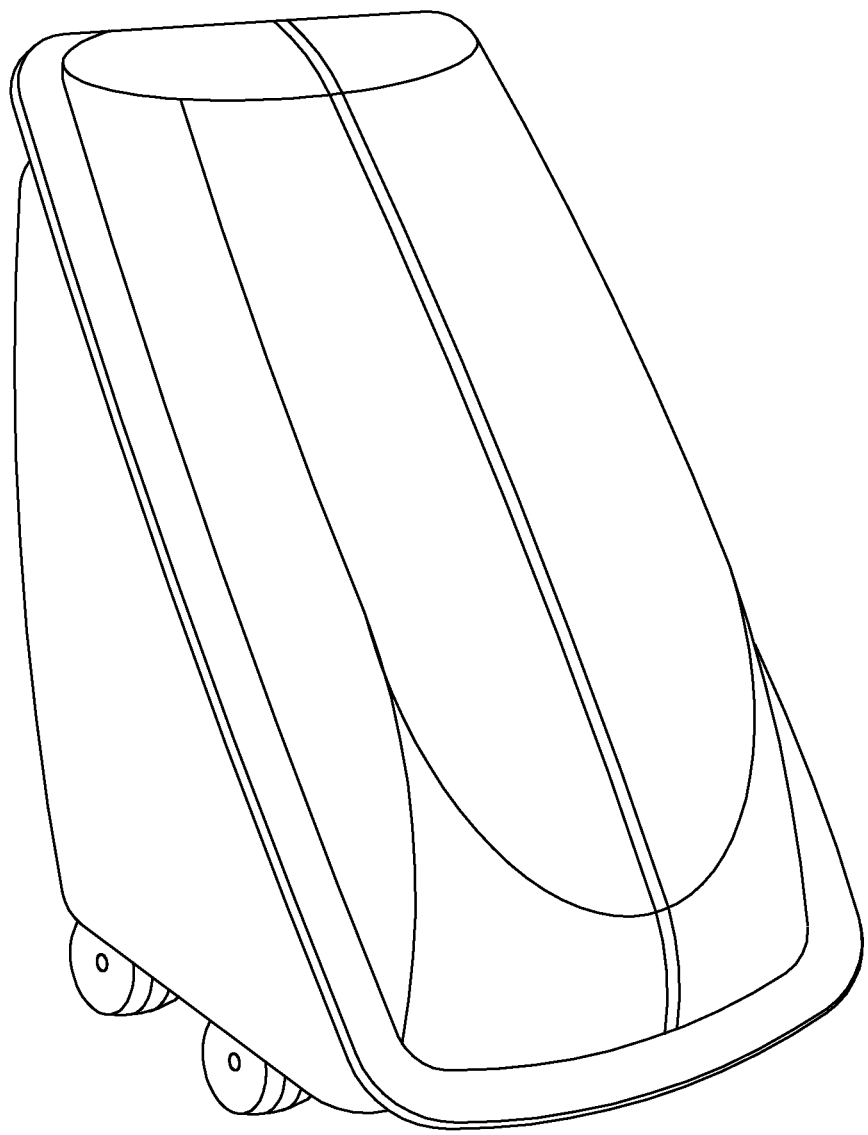
FIGS. 5 and 6 represent an openable transport enclosure.
Figure 6:
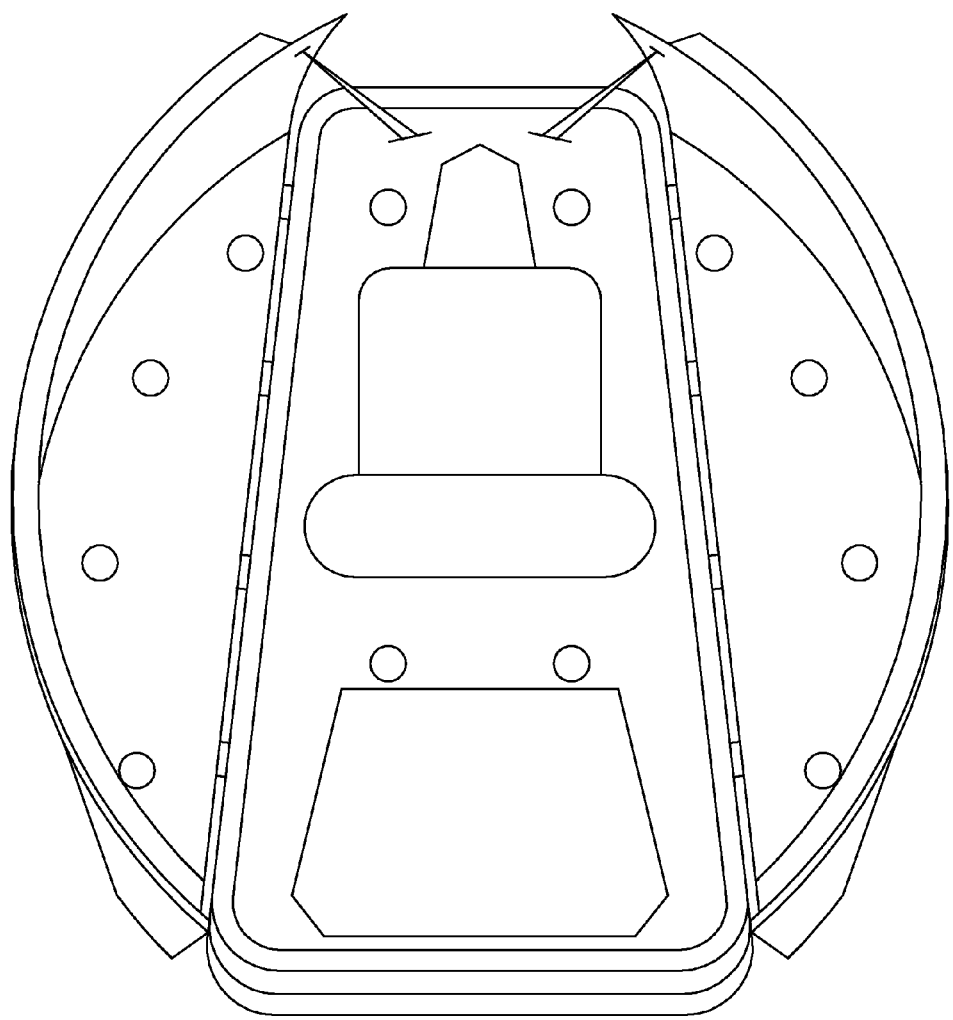

FIGS. 5 and 6 represent an openable transport enclosure. As is shown, the protective case and sterilizable enclosure as is shown, the openable enclosure has a pair of openable doors which can be used to sterilize the robot. The enclosure can have a plurality of wheels which can be used to transport the enclosure. These wheels can be driven or undrive. As shown in FIG. 6, the interest of the cavity can have a plurality of UV emitters, and an ion production source. The power source of the enclosure can be for example an SMFIR and OLEV technology. The according to the teachings above, the robot or robot caddie can be controlled by the operator with wired or wireless 3-d vision goggles which can be used to control either. Motion detectors and controllers can be used to turn either on or off on a schedule Optionally, the base module can be bi-pedal, or other type of base platforms for movement and navigation. Examples of these include wheels and track treads, interchangeable motion bases, bi-pedal, pedestal and omni directional wheel bases. The system can include inertial sensors, and robot inclination to improve disinfection. The mobile system can include sensors to allow electromagnetic spectrum, sound, touch, chemical sensors (smell, odor), and temperature. The robot is able to sample occurrences in the environment and integrate the information to determine next action by robot. The sensors can gather environmental information and allow the robot to function more autonomously and optimize disinfection. Some power requirements for the robot can be supplied via wireless power transfer.

The robot can be applied to hospital and food processing environments. Internal fiber optic communication can be used to communicate between various modules. Robots can dock together to transfer power or wireless power transfer between robots. Optionally, the mobile platform can incorporate sensors which will allow the mobile platform to avoid obstacles and allow the mobile platform to be controlled by smart phone and apps. The optical tracking system can include a laser 3D depth range finder, or 360 degree vision with miniature cameras connected to emulate an insect's panoramic-vision and a bar code reader.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the Figure s. Spatially relative terms may be intended to encompass different orientations of the device in use or operation in addition to the orientation depicted in the Figure s. For example, if the device in the Figure s is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A robot platform for remotely controlled and/or autonomous disinfection of technical facilities, comprising:
    a drive mechanism configured to move the robot platform;
    a first disinfection module having a plurality of UV emitters disposed above the drive mechanism and selectively engagable shields which function to block the application of UV radiation in a specific direction, the disinfection module further having an articulating arm which has a second associated disinfecting module, the articulating arm has an actuator which can direct the emissions from the second disinfecting module, first disinfection module configured to disinfect the technical facility; and
    a position determination device configured to determine position data of the robot platform and a communication device configured to exchange control data and transmission of measurement and position data to an evaluation unit.

2. The robot platform as claimed in claim 1, wherein the robot platform is comprised of individual modules which are physically connected to one another by mechanical connectors.

3. The robot platform as claimed in claim 2, wherein the first disinfection module comprises a plurality of U.V. light sensors.

4. The robot platform as claimed in claim 2, wherein one of the modules is a linear movement module for linear movement of a disinfection device.

5. The robot platform as claimed in claim 1, further comprising a plurality of range sensors.

6. The robot platform as claimed in claim 5, wherein the range of sensors are selected from the group of ultrasonic transceivers, laser transceivers, infra-red transceiver and optical sensor.

7. The robot platform as claimed in claim 6, comprising a submodule interfaced for data exchange and a power supply link between the modules.

8. The robot platform as claimed in claim 7, wherein the individual modules have an electric drive motor and an integrated control unit for the electric drive motor the control unit having a power submodule and a microcontroller submodule as submodules.

9. The robot platform as claimed in claim 6, wherein one of the modules is a base station, which is configured to control data exchange of disinfection signals with the other modules and an evaluation unit.

10. The robot platform as claimed in claim 9, further comprising a device, configured to coordinate transformation of position data, provided upstream of the evaluation unit, such that the evaluation unit can operate in a freely selectable coordinate system which is matched to the disinfection to be carried out.

11. The robot platform as claimed in claim 1, wherein at least one of the modules is a drive module for movement of the robot platform.

12. The robot platform as claimed in claim 11, wherein the drive module has an electric drive motor and, as submodules, comprises at least one wheel for rolling on a surface of the technical facility to be disinfected, a power submodule for supplying power to the drive motor, and a microcontroller submodule for controlling the disinfecting module.

13. The robot platform as claimed in claim 1, wherein at least one of the modules is configured to determine a position of the robot platform.

14. The robot platform as claimed in claim 13, wherein a position transmitter submodule is provided to determine the position, and has a position transmitter wheel and an encoder unit.

15. A robot platform for remotely controlled and/or autonomous disinfection of technical facilities, comprising:

a drive mechanism configured to move the robot platform;

a first disinfection module configured to disinfect the technical facility having a plurality of UV light emitters disposed above the drive mechanism the first disinfection module having selectively engagable shields which function to block the application of UV radiation in a specific direction, the disinfection module further having an articulating arm which has a second associated disinfecting module, the articulating arm has an actuator which can direct the emissions from the second disinfecting module; and a position determination device configured to determine position data of the robot platform and a communication device configured to exchange control data and transmission of measurement and position data to an evaluation unit, wherein the robot platform is comprised of individual modules which are physically connected to one another by mechanical connectors.

16. The robot platform as claimed in claim 15, further comprising a plurality of range sensors.

* * * * *